(12) United States Patent
Abdourazak et al.

(10) Patent No.: US 6,919,160 B2
(45) Date of Patent: Jul. 19, 2005

(54) ACRYLIC COMPOUNDS FOR SUB-200 NM PHOTORESIST COMPOSITIONS AND METHODS FOR MAKING AND USING SAME

(75) Inventors: Atteye Houssein Abdourazak, Allentown, PA (US); Thomas John Markley, Blandon, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 58 days.

(21) Appl. No.: 10/371,251

(22) Filed: Feb. 20, 2003

(65) Prior Publication Data

US 2004/0175644 A1 Sep. 9, 2004

(51) Int. Cl.$^7$ .......................... G03F 7/039; C08F 18/20; C07D 315/00
(52) U.S. Cl. .................... 430/270.1; 430/907; 430/914; 526/246; 549/417; 549/423
(58) Field of Search .............................. 430/270.1, 907, 430/914; 526/246; 549/417, 423

(56) References Cited

U.S. PATENT DOCUMENTS

| | | |
|---|---|---|
| 6,291,130 B1 | 9/2001 | Kodama et al. .......... 430/270.1 |
| 6,406,828 B1 | 6/2002 | Szmanda et al. ........ 430/270.1 |
| 2002/0004570 A1 | 1/2002 | Zampini et al. ............ 526/257 |
| 2002/0051936 A1 | 5/2002 | Harada et al. ........... 430/270.1 |
| 2002/0055060 A1 | 5/2002 | Taylor et al. ............ 430/270.1 |
| 2002/0061464 A1 | 5/2002 | Aoai et al. ............... 430/270.1 |

FOREIGN PATENT DOCUMENTS

| | | |
|---|---|---|
| EP | 1103856 | 5/2001 |
| EP | 1126322 | 8/2001 |
| WO | WO 0017712 | 3/2000 |
| WO | WO 0067072 | 11/2000 |
| WO | WO 0163362 | 8/2001 |
| WO | WO 0185811 | 11/2001 |
| WO | WO 0221212 | 3/2002 |
| WO | WO 0221213 | 3/2002 |
| WO | WO 0221214 | 3/2002 |
| WO | WO 0221216 | 3/2002 |

OTHER PUBLICATIONS

M. M. Dhingra, et al. "Polymerization of 1,1,1 Trifluoroacetone with Aliphatic Secondary Amines. A Proton and Fluorine Magnetic Resonance Invesitgation,"Organic Magnetic Resonance, vol. 9, No. 1 (1977), pp. 23–28.

H. E. Simmons, et al., "Fluoroketones" The Central Research Department Station, E. I. du Pont de Nemours and Co., vol. 82 (1959), pp. 2288–2296.

E. T. McBee, et al., "The Chemistry of 1,1,1–Trifluoropropanone. II. The Reactions of 4–Methyl–1,1,1,–5,5, 5–hexafluoro–3–penten–2–one with Methyimagnesium Iodide," The Department of Chemistry, Purdue University (1956), pp. 4597–4598.

A. L. Henne, et al., "Trifluoromethylated Butadienes," The Department of Chemistry at The Ohio State University (1954), pp. 5147–5148.

K. J. Pryzbilla, et al., "Mexafluoroacetone in Resist Chemistry: A Versatile New Concept for Materials for Deep UV Lithography," SPIE Advances in Resist Chemistry and Process IX vol. 1672 (1992).

M. K. Crawford, et al., "New Materials for 157 mn Photoresists: Characterization and Properties," SPIE Advances in Resist Chemistry and Processing IX vol. 3999 (2000).

R. R. Dammel, et al., "New Resin Systems for 157 nm Lithography," Journal of Photopolymer Science and Technology, vol. 14 No. 4 (2001).

H. Ito, et al., "Development of 157 nm Positive Resists," J. Vac. Sci. Technol. B 19(6) (2001).

H. Ito, "Dissolution Behavior of Chemically Amplified Resist Polymers for 248–, 193–, and 157–nm Lithography," J. Res. & Dev. vol. 45 No. 5 (2001).

S. Cho, et al., "Investigation of a Fluorinated ESCAP based resist for 157 nm Lithography," (2001).

K. Patterson, et al., "The Challenges in Materials Design for 157 nm Photoresists," Lithography, Solid State Technology, pp. 41–48 (2000).

*Primary Examiner*—Richard L. Schilling
(74) *Attorney, Agent, or Firm*—R. P. Morris-Oskanian

(57) ABSTRACT

Disclosed herein is an acrylic compound that can be polymerized by itself or with at least one other ethylenically unsaturated monomer to provide a polymer. The polymer may be used, for example, within a sub-200 nm photoresist composition. Also disclosed is a method to make the acrylic compound of the present invention from the raw material trifluoroacetone.

26 Claims, No Drawings

ACRYLIC COMPOUNDS FOR SUB-200 NM PHOTORESIST COMPOSITIONS AND METHODS FOR MAKING AND USING SAME

BACKGROUND OF THE INVENTION

The present invention relates generally to an acrylic compound. This invention also relates to the use of these compounds, for example, as monomers that can be homopolymerized or copolymerized with other monomers to make resins within sub-200 nanometer (nm) photoresist compositions.

Photoresists are photosensitive films that are used for the transfer of images to a substrate. In a typical lithography process, a substrate is generally coated with either a positive or negative photoresist coating. The photoresist-coated substrate is then exposed through a photomask to an activating radiation source which transfers the pattern of the photomask onto the photoresist-coated substrate. Depending upon whether the photoresist coating is positive or negative, the radiation source either increases or decreases its solubility in a subsequently applied, alkaline developer solution. In a positive photoresist coating, the areas masked from the radiation source remain after development while the exposed areas are dissolved away whereas in a negative photoresist coating the opposite occurs. The patterned photoresist image acts as a mask for subsequent substrate patterning processes such as etching, doping, and/or coating with metals, other semiconductor materials, or insulating materials.

Current interest in the semiconductor industry has increased in photoresists that can be photoimaged with short wavelength radiation, i.e., exposure radiation of about 200 nm or less such as 193 nm (ArF laser) or 157 nm ($F_2$ excimer beam laser) wavelengths. Short exposure wavelengths may allow for the formation of smaller features within the semiconductor device. In this connection, a photoresist that can provide well-resolved images after exposure to a 193 nm or 157 nm wavelength radiation source may allow for the formation of relatively smaller (e.g., sub-0.25 $\mu$m) features. Smaller device features meet the industry demands for smaller dimension circuit patterns and provide for greater circuit density and enhanced device performance.

Photoresist materials, particularly sub-200 nm materials, are particularly challenging to develop because of the need to balance a variety of different performance characteristics. Photoresist materials should ideally provide high transparency at the exposure wavelength, sufficient resistance to plasma-etching processes, and functional groups that are capable of undergoing sufficient photochemical transformations that change the solubility in developer solutions. Besides these, other important characteristics include, but are not limited to, reasonably simple synthesis procedures, adhesion to the underlying substrate, glass transition temperatures compatible with typical processing temperatures, acceptable shelf storage lifetime, and minimum toxicological risk.

The prior art discloses a variety of monomers that can be polymerized and used as base resins within photoresist compositions for sub-200 nm applications. For the higher end of this range (e.g. 193 nm), cycloaliphatic structures have drawn the most attention. For lower wavelength applications (e.g. 157 nm), the monomers tend to have one or more electron-withdrawing groups such as fluorine or hydroxyl and one or more cyclic structures. It is believed that the combination of the electron-withdrawing groups and the one or more cyclic structures improve the performance of the photoresist composition, particularly transparency. For example, U.S. Patent Application US2002/0004570 ("Zampini I") describes photoresist compositions that contain polymerized units of cyclic olefin monomers having one or more pendant cyclic electron-withdrawing groups. The pendant cyclic electron-withdrawing groups disclosed may be N-based, O-based, or S-based.

European published patent application WO 02/21214 ("Zampini II") discloses base resins within 157 nm photoresist compositions that contain at least one electronegative group that includes aromatic groups such as phenolic moieties. In this connection, Zampini II specifically describes vinyl ether entities that incorporate fluorinated aromatic structures as the electronegative group.

European published patent application WO 02/21213 ("Taylor") describes resins that are used within photoresist compositions that contain photoacid-labile deblocking groups substituted with one or more electron-withdrawing groups. The electron-withdrawing moieties within the resin are bonded to the blocking group so that the acid-catalyzed blocking and deblocking reactions are relatively unaffected by their presence.

Japanese Application JP 2002/179,731 (Chemical Abstracts 137:54625; "Harada I") discloses photoresist resins that contain the structure: $CO_2CR^1R^2R$ where $R^1$ and $R^2$=H, F, or a $C_{1-20}$ alkyl and R=$C_{3-20}$ cyclic alkyl. In addition, Harada I describes an acrylate resin that contains fluorinated alkyl groups in ester side chains.

U.S. Patent Application 2002/0051936 ("Harada II") describes an acrylic resin that contains repeating units containing a fluorinated hydrocarbon group, an acid labile group, and an adhesive group. Harada II describes one of the units, preferably the acid labile group, as having at least one alicyclic structure. Harada II also describes acrylic polymers containing the structure —O—$C(R^1R^2)$—$C(H)(R^3)R^4$, where $R^1$, $R^2$, $R^3$, and $R^4$ are H, F, or an unsubstituted or fluorinated, straight, branched or cyclic alkyl group.

European Application EP 1 126 322 describes resins for use in a 157 nm photoresist that contain fluorinated ester groups.

European Application EP 1,103,856 ("Tsutsumi") describes a fluorine-containing resin that contains polymerized units of an acrylic or methacrylic acid ester wherein the ester moiety comprises a fluorine-containing group. Tsutsumi further describes moieties where the fluorine-containing group has a cyclic structure such as a fluorine-containing benzene ring, a fluorine-containing cyclopentane ring, a fluorine-containing cyclohexane ring, or a fluorine-containing cycloheptane ring.

Photoresist materials currently being developed for 157 nm, such as the materials described above, are difficult to prepare and raw materials are often difficult to work with or not readily available. For example, it is quite common to utilize hexafluoroacetone (HFA) for incorporating hexafluoro-2-propanol groups into the monomers. The hexafluoro-2-propanol groups, which incorporate strong electron-withdrawing groups such as fluorine atoms and hydroxyl groups, offer improved transparency of the materials at that wavelength when compared to its non-fluorinated analogs. Despite its advantages in transparency, hexafluoroacetone itself is a highly toxic gas and may not be readily available as a raw material. Further, other issues, such as selectivity and low yields associated with current manufacturing processes for making these compounds, may make it less practical and cost effective to use HFA-based monomers within photoresist compositions.

An alternative to using a HFA-based monomer within the photoresist material is using a trifluoroacetone-based monomer such as the cyclic trimer; 4,6-dihydroxy-2-methyl-2,4,6-trifluoromethyltetrahydropyran. Current procedures for making the cyclic trimer; 4,6-dihydroxy-2-methyl-2,4,6-trifluoromethyltetrahydropyran cannot be readily adapted to a large scale commercial production. These procedures include the reaction of trifluoroacetone with reactive metals such as sodium (A. L. Henne and P. E. Hinkamp, J. Am. Chem. Soc. 76, 5147, 1954), magnesium-amalgam (S. Resconich, Ph. D. Thesis, Purdue University, 1961), fused potassium hydroxide (D. H. Campbell, Ph. D. Thesis, Purdue University, 1955), chlorohydrin in the presence of potassium carbonate (H. E. Simmons and D. W. Wiley, J. Am. Chem. Soc. 82, 2288, 1960), and anhydrous diethylamine or dipropylamine (M. M. Dhingra and K. R. Tatta, Org. Mag. Res 9 (1), 23, 1977).

Accordingly, there is a need in the art to provide resins polymerized from monomers that are transparent at sub-200nm wavelengths. There is also a need in the art for safe and cost effective industrial processes to make fluorine-containing acrylic monomers at greater yields, less cycle time, lower process temperatures, less volatility, and less toxicity.

All references cited herein are incorporated herein by reference in their entirety.

BRIEF SUMMARY OF THE INVENTION

The present invention is directed, in part, to acrylic compounds and methods of making and using same. Specifically, in one aspect of the present invention, there is provided a compound of the formula (I):

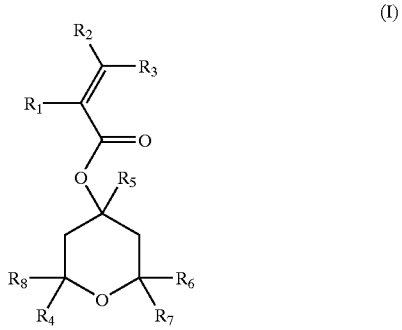

(I)

wherein $R_1$, $R_2$, and $R_3$ are each independently a hydrogen atom, a fluorine atom, an alkyl group, or a fluorinated alkyl group; $R_4$ is a hydroxyl group, an alkoxy group, a fluorinated alkoxy group, an acyloxy group, or a fluorine atom; $R_5$, $R_6$, $R_7$, and $R_8$ are each independently a fluorine atom, a fluorinated alkyl group having from 1 to 10 carbon atoms, an alkyl group, an alkenyl group, an alkynyl group, an aryl group, or an alkyl-substituted aryl group and at least one of $R_5$, $R_6$, $R_7$, and $R_8$ is a fluorinated alkyl group having from 1 to 10 carbon atoms and wherein the alkyl group comprises from 1 to 20 carbons and the alkenyl and alkynyl groups comprise from 2 to 8 carbons.

In a further aspect of the present invention, there is provided a method for making an acrylic compound of the above formula (I) comprising: combining a quantity of trifluoroacetone with a base under conditions sufficient to effect a reaction and form a cyclic trimer intermediate product; and reacting the cyclic trimer intermediate product with an acylating agent under conditions sufficient to form the fluorine-containing compound.

In yet another aspect of the present invention, there is provided a polymer comprising polymerized units of one or more acrylic compounds of the above formula (I).

In a still further aspect of the present invention, there is provided a photoresist composition comprising one or more polymers as described-above and a photoactive compound.

These and other aspects of the invention will become apparent from the following detailed description.

DETAILED DESCRIPTION OF THE INVENTION

The present invention is directed to fluorine-containing acrylic compounds and methods for making and using same in, for example, a photoresist composition. The compound of the present invention may be polymerized by itself to provide a homopolymer or with other ethylenically unsaturated monomers to provide a copolymer. The polymer of the present invention may be used, for example, in a sub-200 nm photoresist composition. The terms "resin" and "polymer" are used interchangeably throughout this specification.

Unlike other monomers used in photoresist resins in the art made from hexafluoroacetone, the fluorine-containing acrylic compounds of the present invention are derived from readily available and easily handled raw materials such as trifluoroacetone or various ketones. In certain preferred embodiments, the trifluoroacetone is reacted with a base to form the intermediate, cyclic trimer 4,6-dihydroxy-2-methyl-2,4,6-trifluoromethyltetrahydropyran prior to the formation of the acrylic compound of the present invention. Due to the prior difficulties in the art in making the cyclic trimer 4,6-dihydroxy-2-methyl-2,4,6-trifluoromethyltetrahydropyran, it is surprising and unexpected to produce fluorine-containing acrylic compounds for use as monomers for photoresist resins at relatively high yields from a readily available material such as trifluoroacetone. In addition, the ability to easily and cleanly make a fluorine-containing acrylic compound in high yield and selectivity from this cyclic trimer is unanticipated, and aids greatly in the economics of producing a viable, highly fluorinated monomer for 157 nm or other applications. This is particularly noteworthy, since the material is a diol and it is generally difficult to cleanly acrylate only at one position in such compounds.

The fluorine-containing acrylic compound of the present invention are of the following general formula (I):

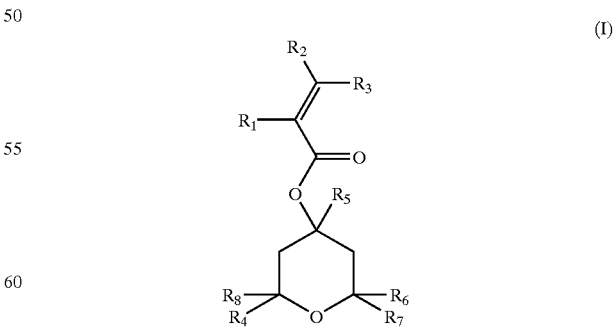

(I)

In formula (I), substituents $R_1$, $R_2$, and $R_3$ may each independently be a hydrogen atom, a fluorine atom, an alkyl group, or a fluorinated alkyl group having from 1 to 20 carbon atoms; $R_4$ may be a hydroxyl group, an alkoxy group, an acyloxy group, a fluorinated alkoxy group, or a fluorine atom; $R_5$, $R_6$, $R_7$, and $R_8$ may each independently be a fluorine atom, a fluorinated alkyl group having from 1 to 10 carbon atoms, an alkyl group, an aryl group, an alkenyl group, an alkynyl group, an aryl group, or an alkyl-substituted aryl group. The term "alkyl" as used herein includes straight chain, branched, or cyclic alkyl groups, preferably containing from 1 to 20 carbon atoms, or more preferably from 1 to 10 carbon atoms. Exemplary alkyl groups include methyl, ethyl, n-propyl, isopropyl, n-butyl, isobutyl, sec-butyl, tert-butyl, tert-amyl, n-pentyl, n-hexyl, cyclopentyl, and cyclohexyl. The term "alkyl" applies also to alkyl moieties contained in other groups such as haloalkyl, alkaryl, or aralkyl. The term "aryl" as used herein includes six to twelve member carbon rings having aromatic character. The term "aryl" also applies to aryl moieties that are substituted. The term "halo" and "halogen" include fluorine, chlorine, bromine, or iodine. The term "fluorinated alkyl" applies to alkyl moieties wherein one or more of its hydrogens are replaced by a fluorine heteroatom, may be partially or fully fluorinated, and includes straight chain, branched or cyclic fluorinated alkyl groups containing from 1 to 20 carbon atoms, or more preferably from 1 to 10 carbon atoms. Exemplary fluorinated alkyl groups include —$CF_3$, —$CF_2CF_3$, —$CF_2CH_3$, —$CF_2CFH_2$, or —$CF_2CH_2CH_3$. In certain embodiments, some of the groups may be substituted with one or more heteroatoms such a halogen atom or other heteroatoms such as O, N, or S. In certain preferred embodiments, at least one of substituents $R_5$, $R_6$, $R_7$, and $R_8$ is a fluorinated alkyl group having from 1 to 10 carbons. In certain preferred embodiments of the present invention, $R_4$ is OH, $R_5$, $R_7$, and $R_8$ are each $CF_3$, and $R_6$ is $CH_3$.

Referring again to formula (I), substituent $R_4$ may be a hydroxyl group, an alkoxy group, an acyloxy group, a fluorinated alkoxy group, or a fluorine atom. In certain embodiments of the present invention, substituent $R_4$ may be an alkoxy group. Exemplary alkoxy groups include $CH_3O$—(methoxy), $CH_3CH_2O$—(ethoxy), $CH_3CH_2CH_2O$—(propoxy), $(CH_3)_2CH$—(isopropoxy), etc. The alkoxy group could also contain additional oxygen atoms, such as $CH_3OCH_2CH_2O$—, $CH_3OCH_2O$—, $CH_3CH_2OCH_2O$—, etc. The alkoxy group may also encompass a cyclic structure such as, for example, the following:

Alternatively, substituent $R_4$ may be a fluorinated alkoxy group. In these embodiments, one or more of its hydrogens are replaced by a fluorine heteroatom. Exemplary fluorinated ether groups include $R_f(CH_2)_nO$— wherein $R_f$ is linear, branched or cyclic perfluorinated or hydrofluorinated chain having $C_1$ to $C_{10}$ and n is a number ranging from 0 to 10. In other embodiments of the present invention, substituent $R_4$ may be an acyloxy group.

The acrylic compound of the present invention is preferably made from trifluoroacetone which is an inexpensive and readily available liquid and does not possess the toxicity issues associated with hexafluoroacetone. In one aspect of the present invention, the compounds of the present invention may be prepared in a two-step process such as the exemplary process shown below:

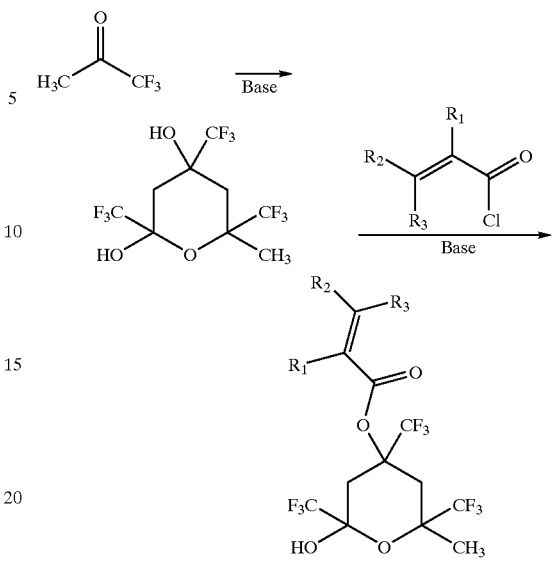

The first step of the process involves the reaction of trifluoroacetone with a strong base (i.e., having a base whose conjugate acid has a $pK_a$ of 10 or greater) such as potassium tert-butoxide to produce an intermediate product which is 4,6-dihydroxy-2-methyl-2,4,6-trifluoromethyltetrahydropyran. The term "base" as used herein is any compound capable of removing an acidic proton and include compounds such as, but not limited to, amine, hydroxide, halide, alkoxide, metal amide, organolithium, or organomagnesium compounds. The base may also be present in the reaction in solid, liquid, or gaseous phase. In one embodiment, heterogeneous reactions in which the base is in solid form may also be used including those involving gas-phase reactions. In other embodiments, the base is in a liquid or gaseous phase and the reaction preferably occurs in the presence of a solvent. In embodiments where a solvent is used, the solvent selected will preferably not substantially react with trifluoroacetone or the intermediate product under the reaction conditions. Suitable solvents include, but are not limited to, halocarbons (e. g. Freon 113); ethers (e. g. diethylether ($Et_2O$), tetrahydrofuran ("THF"), di-n-butyl ether, 1,4-dioxane, or ethylene glycol dimethyl ether); nitriles (e. g. $CH_3CN$); or aromatic compounds (e.g. benzotrifluoride), alone or in admixture thereof. In certain preferred embodiments, the solvent is an ether. The reaction temperature may range from −78° C. to the boiling point of the solvent. The reaction time for the first step may range from about 0 hours or instantaneous to about 48 hours, preferably from about 4 to about 12 hours. The anticipated yield of the intermediate product ranges from about 50% to about 80% of the theoretical yield . The intermediate product may be purified by standard procedures such as distillation, chromatography, recrystallization, and/or trituration.

In the second step, the 4,6-dihydroxy-2-methyl-2,4,6-trifluoromethyltetrahydropyran intermediate product of the first step is reacted with an acylating agent in the presence of a base to form the acrylic compound of the present invention. In this step, the 4-position hydroxyl group of the intermediate product is acylated with one equivalent of the acylating agent. Examples of suitable acylating agents include an acyl halide, an acid anhydride, an ester, or an acid. In some embodiments, the second step may be conducted in the presence of a solvent. Solvents that may be used in the second step include any of the solvents used in the first step. The temperature for the second step may range from −78° C. to the boiling point of the solvent. The reaction time for the second step may range from about 0 to about 12 hours or preferably from about 0.5 to about 4 hours. The anticipated yield of the acrylic compound ranges from about 50% to about 85% of the theoretical yield. The final product may be purified by standard procedures such as distillation, chromatography, recrystallization, and/or trituration.

In certain embodiments of the present invention, the acrylic compound of the present invention may be exposed to a deoxofluorinating agent to replace the 6-position hydroxyl group with a fluorine atom. Deoxofluorinating agents suitable for use in the invention include aminosulfur trifluorides, e.g., diethylaminosulfur trifluoride (DAST), bis (2-methoxyethyl)aminosulfur trifluoride (DEOXOFLUOR™ reagent available from Air Products and Chemicals, Inc., Allentown, Pa.), perfluorobutanesulfonyl fluoride, 2-chloro-1,2,3-trifluoroethyidiethylamine (Yarovenko-Raksha reagent), hexafluoroisopropyl diethylamine (Ishikawa reagent) and pyridine:hydrofluoride, triethylamine:trishydrofluoride. Preferably, the deoxofluorinating agent is bis(2-methoxyethyl)aminosulfur trifluoride. The deoxofluorinating step is preferably conducted in the presence of a solvent such as any of the solvents used in the previous steps. The temperature for the second step may range from −78° C. to the boiling point of the solvent. The reaction time for the second step may range from about 0 to about 12 hours or preferably from about 0 to about 4 hours. As before, the final product may be purified by standard procedures such as distillation, chromatography, recrystallization, and/or trituration.

The acrylic compound of the present invention can be polymerized by itself to provide a homopolymer or with at least one other ethylenically unsaturated polymer to provide a copolymer. The term "homopolymer" as used herein refers to polymers comprised of repeating units of one ethylenically unsaturated compound such as the acrylic compound of the present invention. The term "copolymer" as used herein refers to polymers comprised of repeating units of the acrylic compound of the present invention and polymerized units of at least one ethylenically unsaturated compound and can include, for example, random, alternating, block, star, or graft polymers.

The acrylic compound of the present invention may be polymerized to form a polymer having the following formula (II):

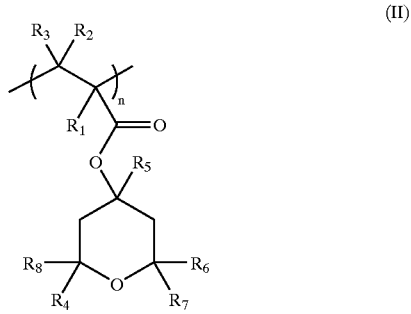

(II)

In formula (II), substituents $R_1$, $R_2$, $R_3$, $R_4$, $R_5$, $R_6$, $R_7$, and $R_8$ are the substituents previously described herein and n is a number ranging from 3 to 300, preferably from 3 to 150, and more preferably from 5 to 30. The formula (II) polymer may further include polymerized units of another ethylenically unsaturated compound to provide a copolymer.

In certain preferred embodiments of the present invention, the acrylic compounds of the present invention may be polymerized with at least one other ethylenically unsaturated momomer to form a resin or polymer. The at least one ethylenically unsaturated monomer may include any of the ethylenically unsaturated monomers commonly known in the art, such as those listed in *The Polymer Handbook,* 3rd Edition, Brandrup and Immergut, Eds., Wiley Interscience, Chapter 2, (1989). Suitable ethylenically unsaturated monomers include, for example, the $C_1$–$C_{18}$ alkyl (meth)acrylate monomers (e.g. methyl-, ethyl-, propyl-, n-butyl-, sec-butyl-, tert-butyl, pentyl-, hexyl-, isobornyl-heptyl-, n-octyl-, 2-ethylhexyl-, decyl-, undecyl-, dodecyl-, lauryl, cetyl, and stearyl-(meth)acrylate and the like); vinyl aromatic monomers (e.g. styrene, para-hydroxystyrene, alpha-methyl styrene, para-methyl styrene, chlorostyrene, vinyl toluene, dibromostyrene, tribromostyrene, fluorostyrene, difluorostyrene, trifluorostyrene, tetrafluorostyrene, pentafluorostyrene, tetrafluorohydroxystyrene, vinyl naphthalene, isopropenyl naphthalene, divinylbenzene and the like); vinyl esters (e.g., vinyl acetate; vinyl versatate; and the like); vinyl-unsaturated carboxylic acids monomers (e.g., methacrylic acid, acrylic acid, maleic acid, itaconic acid); nitrogen-containing vinyl unsaturated monomers (e.g., acrylonitrile, methacrylonitrile, and $C_1$–$C_{18}$ alkyl (meth)acrylamides, and the like); dienes (e.g., butadiene, isoprene, and norbornadiene); ethylene, norbornene, hydroxyethyl(meth)acrylate, hydroxypropyl(meth)acrylate, and the like. The term "(meth)acrylate", as used herein, refers to both esters of methacrylate and acrylate.

Other suitable ethylenically unsaturated monomers for copolymerization with the acrylic compound of the present invention are fluorinated olefins, such as mono-, di-, tri-, and tetrafluoroethylene. Similarly, partially and fully fluorinated derivatives of propylene, butylene, and isobutylene would be suitable co-polymers, as would fluorinated derivatives of maleic anhydride, fluoro-(meth)acrylates (vinyl substituted), and fluoro-methacrylates (methyl substituted). Other usable monomers are shown below:

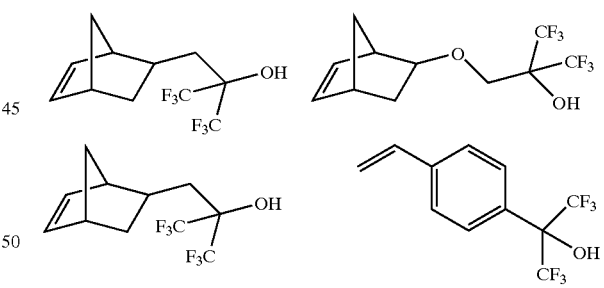

A particularly useful embodiment would be the utilization of co-monomers that contain acid-labile groups to facilitate the development of these materials when used in photoresists. The co-monomer structure can be generally described as A-O-PG, where A- is a polymerizable fragment that influences the oxygen such that A-OH would be acidic ($pK_a$ <12) and PG is a protecting group that can be removed under the influence of acid (i.e. from a photoacid generator). Suitable examples of A would be (meth)acryloyl groups as described above, and suitably fluoro-substitutued alkyl groups (also described above). Examples of PGs would be tertiary alkoxy groups (for when A-O-PG is an ester), tert-alkoxycarbonyl groups, alkoxy methyl groups of type —OCHR$_5$OR$_6$ (including cyclic derivatives where R$_5$ and $R_6$ are joined together in a ring). Specific individual monomers of type A-O-PG are shown below:

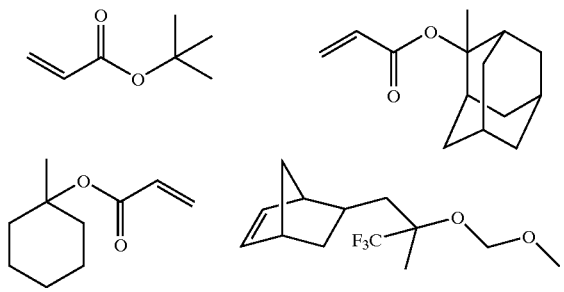

It is also possible to have the protecting group incorporated in such as fashion so as to be non-fragmenting (see below):

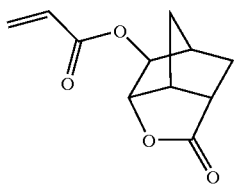

A polymer may be prepared using the acrylic compound as a monomer, and optionally at least one other ethylenically unsaturated monomer, using a typical polymerization process such as bulk polymerization, solution polymerization, batch polymerization, suspension polymerization or emulsion polymerization. The polymerization reaction can be initiated by a free-radical polymerization intiator or a metal catalyst. Any initiator or catalyst is suitable for use in the present invention as long as it catalyzes the polymerization of the double bond without substantially opening the ring of the acrylic compound monomer. In general, the polymerization reaction may be conducted by combining one or more the monomers to form a reaction mixture, adding a metal catalyst or polymerization initiator to the reaction mixture, and effecting polymerization reaction while heating or cooling the system if necessary. The time and temperature conditions for the polymerization reaction to occur depend upon a variety of factors such as whether solvent is used within the reaction mixture, whether a metal catalyst or polymerization initator is used, trigger means (i.e., light, heat, radiation, plasma, etc.), polymerization conditions (i.e., temperature, pressure, solvent, concentration, and additives), and the like.

In embodiments where a free-radical polymerization initiator is used, suitable initators include, but are not limited to, Vazo initiators such as 2, 2' azobis(isobutyronitrile) (AIBN), hydrogen peroxide, tert-butyl hydroperoxide, sodium persulfate, potassium persulfate, lithium persulfate; and the like. In alternative embodiments, a metal polymerization catalyst may be used. Suitable metal polymerization catalysts include, but are not limited to, palladium(II) catalysts or nickel (II) catalysts.

The polymer of the present invention has a number average molecular weight that ranges from 500 to 50,000, preferably from 750 to 25,000, and more preferably from 1,000 to 15,000, as determined by gel chromatography. The glass transition temperature of the polymer of the present invention, as determined by differential scanning calorimetry (DSC), ranges from 40 to 200, preferably from 60 to 180, and more preferably from 80 to 160.

A photoresist compositon may be formulated using as the base resin the polymer resulting from polymerization of the acrylic compound of the present invention and optionally one or more ethylenically unsaturated monomers. A typical photoresist composition comprises a polymer, a photoactive compound, optionally a crosslinker, optionally a basic compound, optionally a dissolution inhibitor, and optionally other additives such as, but not limited to, anti-striation agents, plasticizers, speed enhancers, fillers, dyes, and the like within a solvent medium. Typically, the solids content of the photoresist composition varies from about 5 to about 35 percent by weight, based on the total weight of the composition. The polymer and photoactive component should be present in amounts sufficient to provide a film coating layer and formation of good quality latent and relief images. Optional additives will be present in relatively minor concentrations in the photoresist composition except for fillers and dyes which may be used in relatively large concentrations, e.g. in amounts of from about 5 to 30 percent by weight, based on the total weight of solids within the composition.

The photoactive compound is typically added to the photoresist composition in an amount sufficient to generate a latent image in a coating layer of resist material upon exposure to activating radiation. The photoactive compounds useful in the present invention are typically photoacid or photobase generators, and are preferably photoacid generators ("PAG"). The photoacid generators useful in the present invention are any compound which liberates acid upon exposure to light, typically at a wavelength of 300 nanometers or less. Suitable photoacid generators include halogenated triazines, onium salts, sulfonated esters and halogenated sulfonyloxy dicarboximides. When the photoactive compound is a photoacid generator, the amount is typically in the range of 0.1 to 10 percent by weight, based on the weight of the resin, and preferably 1 to 8 percent by weight. It will be appreciated by those skilled in that art that more than one photoacid generator may be used advantageously in the photoresist compositions of the present invention.

Onium salts with weakly nucleophilic anions are particularly suitable for use as photoacid generators in the present invention. Examples of such anions are the halogen complex anions of divalent to heptavalent metals or non-metals, for example, antimony, tin, iron, bismuth, aluminum, gallium, indium, titanium, zirconium, scandium, chromium, hafnium, copper, boron, phosphorus and arsenic. Examples of suitable onium salts include, but are not limited to: diaryl-diazonium salts and onium salts of group VA and B, IIA and B and I of the Periodic Table, for example, halonium salts, quaternary ammonium, phosphonium and arsonium salts, aromatic sulfonium salts and sulfoxonium salts or selenium salts. Examples of suitable onium salts are disclosed in U.S. Pat. Nos. 4,442,197; 4,603,101; and 4,624,912, all incorporated herein by reference. The sulfonated esters useful as photoacid generators in the present invention include sulfonyloxy ketones. Suitable sulfonated esters include, but are not limited to: benzoin tosylate, t-butylphenyl alpha-(p-toluenesulfonyloxy)-acetate, and t-butyl alpha-(p-toluenesulfonyloxy)acetate. Such sulfonated esters are disclosed in the Journal of Photopolymer Science and Technology, vol. 4, No. 3,337–340 (1991), incorporated herein by reference.

The photoresist compositions of the present invention may be readily prepared by those skilled in the art. For example, a photoresist composition of the invention can be prepared by dissolving the components of the photoresist composition in a suitable solvent. Such suitable solvents include, but are not limited to: ethyl lactate, ethylene glycol monomethyl ether, ethylene glycol monomethyl ether acetate, propylene glycol monomethyl ether, propylene glycol monomethyl ether acetate, 3-ethoxyethyl propionate, 2-heptanone, and mixtures thereof.

Such photoresist compositions may be applied to a substrate by any known means, such as spinning, dipping, roller coating and the like. When the compositions are applied by spin coating, the solids content of the coating solution can be adjusted to provide a desired film thickness based upon the specific spinning equipment utilized, the viscosity of the solution, the speed of the spinner and the amount of time allowed for spinning.

Photoresist compositions including the polymers of the present invention are useful in all applications where photoresists are typically used. For example, the compositions may be applied over silicon wafers or silicon wafers coated with silicon dioxide for the production of microprocessors and other integrated circuit components. Aluminum-aluminum oxide, gallium arsenide, ceramic, quartz, copper, glass and the like are also suitable employed as substrates for the photoresist compositions of the invention.

Once the photoresist composition is coated on a substrate surface, it is dried by heating to remove any solvent. It is preferably dried until the coating is tack free. Thereafter, it is imaged through a mask in a conventional manner. The exposure is sufficient to effectively activate the photoacid component of the photoresist composition to produce a patterned image in the resist coating layer, and more specifically, the exposure energy typically ranges from about 1 to 100 $mJ/cm^2$, dependent upon the exposure tool and the components of the photoresist composition.

The photoresist compositions of the present invention are preferably activated by a short exposure wavelength, particularly a sub-300 nm, such as UV, and more preferably a sub-200 nm exposure wavelength. Particularly preferred wavelengths include 248, 193, and 157 nm. However, the photoresist compositions of the present invention may be used at higher wavelengths, such as, but not limited to, visible, e-beam and x-ray.

The invention will be illustrated in more detail with reference to the following examples, but it should be understood that the present invention is not deemed to be limited thereto. The G.C.M.S. Spectra for the examples were performed on a Hewlett Packard 5890 Series 11 G.C. and 5972 series mass selective detector with a 50 meter HP-5MS capillary column. The nuclear NMR analyses for the examples were obtained on a Bruker CP-500FT spectrometer operating at 470.68 MHz ($^{19}F$), 500.28 MHz ($^1H$). Chemical shifts were referenced to neat in $CFCl_3$($^{19}F$) and $CHCl_3$ ($^1H$).

EXAMPLES

Example 1

Preparation of 4,6-dihydroxy-2-methyl-2,4,6-tris (trifluoromethyl)-tetrahydropyran In a 500 mL three-neck round bottom flask equipped with a teflon stirrer, a thermocouple and a nitrogen inlet, 88 mL of a 1M THF solution of potassium tert-butoxide were cooled to a temperature ranging from −30° to −50° C. A 40 mL quantity of trifluoroacetone was slowly added to the flask to form a reaction mixture and the reaction mixture was allowed to warm up to room temperature. After four hours, the reaction mixture was poured onto a dilute solution of hydrochloric acid and the aqueous layer was extracted with ethyl ether. The combined organic layers were dried and filtered and the solvent was evaporated to provide 36 grams of a white solid product after recrystallization from a hexane solvent. The percentage yield of the product was 73%. An analysis of the product identified it as 4,6-dihydroxy-2-methyl-2,4,6-tris(trifluoromethyl)-tetrahydropyran (four stereoisomers, one major). The mass spectrum and NMR results for the product were as follows: mass spectrum m/z (267, M-$CF_3$), $^1H$ NMR of the major component ($CD_3OD$, ppm) 4.86 (s, 2H), 1.79 (s, 3H), 1.84–186 (d, 1H), 1.91–1.94 (d, 1H), 1.97–2.00 (d, 1H), 2.1–2.17 (d, 1H); $^{19}F$ NMR of the major component ($CD_3OD$, ppm) −89.2 (s, CF3), −87.3 (s, CF3), −87.1 (s, CF3).

Example 2

General Procedure for the Acylation Reactions; Preparation of 4,6-hydroxy-2-methyl-2,4,6-tris (trifluoromethyl)-tetrahydropyran-4-acrylic acid ester In a 500 mL three-neck round bottom flask equipped with a teflon stirrer, a thermocouple and a nitrogen inlet, a solution containing 50.26 g of 4,6-dihydroxy-2-methyl-2,4,6-trifluoromethyl-tetrahydropyran (prepared in accordance with Example 1) and 45.7 mL of N-ethyl morpholine in 150 mL of THF was cooled to −15° C. An acylating agent, acryloyl chloride (14.5 mL), was slowly added to form a reaction mixture and the reaction mixture was allowed to warm up to room temperature. After four hours, the reaction mixture was poured onto a dilute solution of hydrochloric acid and the aqueous layer extracted with ethyl ether. The combined organic layers were dried and filtered and the solvent evaporated to provide 47 grams of a white solid product after recrystallization from hexane. The percentage yield of the product was 80.5%. An analysis of the product identified it as 4,6-hydroxy-2-methyl-2,4,6-tris (trifluoromethyl)-tetrahydropyran-4-acrylic acid ester (four stereoisomers, one major). The mass spectrum and NMR results for the product were as follows: mass spectrum m/z (372, M-$H_2O$), $^1H$ NMR ($CD_3OD$, ppm) 6.4–6.5 (dd, 1H), 6.16–6.19 (dd, 1H), 5.93–5.95 (dd, 1H), 4.82 (s, 1H), 3.43–3.46 (dd, 1H), 2.50–253 (dd, 1H), 2.05–2.09 (d, 1H), 1.86–1.88 (d, 1H), 1.72 (s, 3H). $^9F$ NMR ($CD_3OD$, ppm) −80.15 (s, CF3), −86.97 (s, CF3), −88.90 (s, CF3).

Example 3

General Procedure for the Deoxofluorination Reactions; Preparation of 6-fluoro-4-hydroxy-2-methyl-2,4,6-tris(trifluoromethyl)-tetrahydropyran 4-acrylic acid ester In a 50 mL three-neck round bottom flask equipped with a teflon stirrer, a thermocouple and a nitrogen inlet, a solution of 3.9 g of 4,6-dihydroxy-2-methyl-2,4,6-trifluoromethyl-tetrahydropyran-4-acrylic acid ester (prepared in accordance with Example 2) in 8 mL of ethyl ether was slowly added to a cooled solution of bis(2-methoxyethyl)aminosulfur trifluoride (2 mL) in 8 mL of ether to form a reaction mixture. The reaction mixture was allowed to warm up to room temperature. After one hour, the reaction mixture was poured onto a solution of sodium bicarbonate and the aqueous layer was extracted with ethyl ether. The combined organic layers were dried, filtered and the solvent evaporated to give 3.2 g of an oil. The percentage yield of the product was 78%. An analysis of the oil determined that it was 6-fluoro-4-hydroxy-2-methyl-2,4,6-tris(trifluoromethyl)-tetrahydropyran-4-acrylic acid ester (two isomers in a 70:30 ratio). The mass spectrum and NMR results for the product were as follows: mass spectrum m/z (412, M+), $^1$H NMR (CDCl$_3$, ppm) 6.36–6.45 (m, 1H), 6.02–6.10 (m, 1H), 5.89–5.94 (m, 1H) 2.99–3.04 (m, 1H), 2.80–2.90 (dd, 1H), 2.56–2.68 (dd, 1H), 1.50 (s, 3H); $^{19}$F NMR (CDCl$_3$, ppm) −74.13 (s, 0.3 CF3), −79.83 (s, 0.3 CF3), −79.94 (s, 0.7 CF3), −84.43 (s, 0.3 CF3), −84.93 (s, 0.7 CF3), −86.50 (s, 0.7 CF3), −108.62−−108.68 (bm, CF).

Example 4

Polymerization of Monomer (4,6-hydroxy-2-methyl-2,4,6-tris(trifluoromethyl)-tetrahydro pyran-4-acrylic acid ester)

The (4,6-hydroxy-2-methyl-2,4,6-tris(trifluoromethyl)-tetrahydro pyran-4-acrylic acid ester) monomer was prepared in accordance with Example 2. A 2 gram (0.0051 mole) amount of monomer was mixed with 2.65 g of tetrahydrofuran and 21 mg (0.00013 mole) of the initiator, 2,2' azobis(isobutyronitrile) (AIBN) to provide a reaction mixture. Oxygen was removed on a vacuum line in 3 freeze-thaw cycles. The polymerization reaction of the monomer was conducted by heating the reaction mixture to 65° C. under a N$_2$ atmosphere for a 21 to 24 hour period. The reaction product was obtained by removing the solvent on a rotary evaporator. The product was then dried in a vacuum oven under a slight nitrogen purge (50° C., 18 mmHg) overnight to give a white polymer (2.08 g, 104%), indicating not all the solvent was removed. $^{13}$C NMR was run on the product and no free monomer was detected. The molecular weight of the polymer was M$_N$=2,700, M$_W$=3,300.

A DSC analysis of the polymer was run on a TA Instruments Model 2920 instrument at a heat rate of 20° C./min. The product was made into samples that were cycled on the DSC twice, with quenching at −50° C. between cycles. The glass transition temperature (T$_g$) was determined on the second cycle to be 82° C. This polymer was not base soluble in 0.26N tetramethylammonium hydroxide (TMAH) under normal processing conditions. This polymer has a contact angle of 95–100 with water and a contact angle of 80° with 0.26N TMAH. A thin film of this polymer was determined to have an absorption coefficient of 1.9 μm$^{-1}$ by vacuum ultraviolet variable angle spectroscopic ellipsometery (VUV-VASE, measurements performed by J. A. Woollam Co., Inc., Lincoln, Nebr.)

Example 5

Copolymerization of 4,6-Hydroxy-2-methyl-2,4,6-tris(trifluoromethyl)-tetrahydro pyran-4-Acrylic Acid Ester Monomer with 2-Methyladamantyl methacrylate Monomer The (4,6-hydroxy-2-methyl-2,4,6-tris(trifluoromethyl)-tetrahydro pyran-4-acrylic acid ester) monomer was prepared in accordance with Example 2. A 2.5 gram (0.0064 mole) quantity of (4,6-hydroxy-2-methyl-2,4,6-tris(trifluoromethyl)-tetrahydro pyran-4-acrylic acid ester) and a 1 gram (0.0043 mole) quantity of 2-methyladamantyl methacrylate were combined with 4.64 gram of tetrahydrofuran and 43.9 milligram (0.00027 mole) of 2,2' azobis(isobutyronitrile) (AIBN) to form a reaction mixture. Oxygen was removed on a vacuum line using three freeze-thaw cycles. The polymerization reaction was conducted by heating the reaction mixture to 65° C. under a N$_2$ atmosphere for a 21 to 24 hour period. The reaction product was obtained by removing the solvent on a rotary evaporator. The product was then dried in a vacuum oven under a slight nitrogen purge (50° C., 18 mmHg) overnight to give a white polymer. The molecular weight of the polymer was M$_n$=4650, M$_w$ 10,900.

A DSC analysis of the polymer was run on a TA Instruments Model 2920 instrument at a heat rate of 20° C./min. The product was made into samples that were cycled on the DSC twice, with quenching at −50° C. between cycles. The glass transition temperature (T$_g$) was determined on the second cycle to be 97.5° C.

Example 6

Lithographic Screening of Co-Polymer

A copolymer was prepared in accordance with Example 5 and was shown to be photo-labile in the following manner. A 0.168 gram amount of copolymer was dissolved in a mixture containing 1.28 grams of propylene glycol methyl ether acetate (PGMEA) and 0.5 wt % triphenylsulfonium triflate as the PAG. The concentration of copolymer within the PGMEA mixture was 11.6 wt %. The mixture was deposited onto a silicon wafer via spin-coating at a speed of 2000 rpm to form a thin film, followed by a post-applied-bake at 130° C. for 90 seconds. The film was partially exposed to a Fusion UV Systems, Inc. Model F300 continuous wave ultraviolet lamp equipped with a D bulb for approximately 2 seconds followed by a post exposure bake at 118° C. for 90 seconds After exposure, the film was then placed in a 0.26 N TMAH basic solution for approximately 30 seconds. The wafer was removed from the solution and washed with deionized water. The region of the film that was exposed to UV light dissolved in the basic solution whereas the region not exposed to light did not. This demonstrates that the copolymer of the present example can be used as a photoresist.

While the invention has been described in detail and with reference to specific examples thereof, it will be apparent to one skilled in the art that various changes and modifications can be made therein without departing from the spirit and scope thereof.

We claim:

1. An acrylic compound represented by the formula:

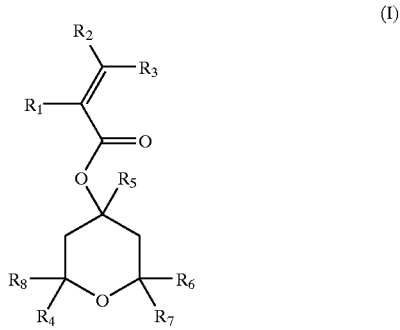

(I)

wherein R$_1$, R$_2$, and R$_3$ are each independently a hydrogen atom, a fluorine atom, an alkyl group, or a fluorinated alkyl group; R$_4$ is a hydroxyl group, an alkoxy group, a fluorinated alkoxy group, an acyloxy group, or a fluorine atom; R$_5$, R$_6$, R$_7$, and R$_8$ are each independently a fluorine atom, a fluorinated alkyl group having from 1 to 10 carbon atoms, an alkyl group, an alkenyl group, an alkynyl group, an aryl group, or an alkyl-substituted aryl group, and at least one of R$_5$, R$_6$, R$_7$, and R$_8$ is a fluorinated alkyl group having from 1 to 10 carbon atoms; and wherein the alkyl group comprises from 1 to 20 carbons and the alkenyl and alkynyl groups comprise from 2 to 8 carbons.

2. The compound of claim 1 wherein R$_5$, R$_7$, and R$_8$ are each a fluorinated alkyl group.

3. The compound of claim 2 wherein R$_5$, R$_7$, and R$_8$ are each CF$_3$.

4. The compound of claim 1 wherein R$_6$ is an alkyl group.

5. The compound of claim 4 wherein R$_6$ is CH$_3$.

6. The compound of claim 1 wherein R$_4$ is a hydroxyl group.

7. The compound of claim 1 wherein R$_5$, R$_7$, and R$_8$ are each CF$_3$, R$_6$ is CH$_3$, and R$_4$ is a hydroxyl group.

8. A method for preparing an acrylic compound of the formula (I):

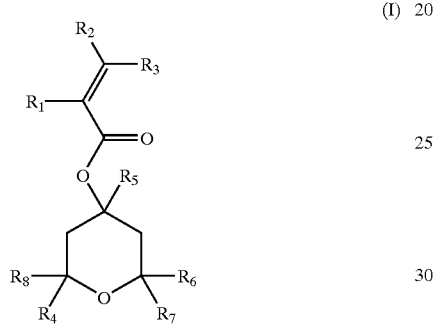

wherein R$_1$, R$_2$, and R$_3$ are each independently a hydrogen atom, a fluorine atom, an alkyl group, or a fluorinated alkyl group; R$_4$ is a hydroxyl group, an alkoxy group, a fluorinated alkoxy group, an acyloxy group, or a fluorine atom; R$_5$, R$_6$, R$_7$, and R$_8$ are each independently a fluorine atom, a fluorinated alkyl group having from 1 to 10 carbon atoms, an alkyl group, an alkenyl group, an alkynyl group, an aryl group, or an alkyl-substituted aryl group and at least one of R$_5$, R$_6$, R$_7$, and R$_8$ is a fluorinated alkyl group having from 1 to 10 carbon atoms; and wherein the alkyl groups comprise from 1 to 20 carbons and the alkenyl and alkynyl groups comprise from 2 to 8 carbons, the method comprising:

combining a quantity of trifluoroacetone with a base under conditions sufficient to effect a reaction and form a cyclic trimer intermediate product; and reacting the cyclic trimer intermediate product with an acylating agent under conditions sufficient to form the acrylic compound.

9. The method of claim 8 further comprising exposing the acrylic compound to a deoxofluorinating agent.

10. The method of claim 9 wherein the deoxofluorinating agent is at least one member selected from the group consisting of diethylaminosulfur trifluoride, bis(2-methoxyethyl) aminosulfur trifluoride, perfluorobutane-sulfonyl fluoride, 2-chloro-1,2,3-trifluoroethyldiethylamine, and hexafluoroisopropyl diethylamine.

11. The method of claim 8 further comprising polymerizing the acrylic compound with at least one ethylenically unsaturated monomer for a time and at least one temperature sufficient to react and to form a polymer.

12. The method of claim 8 further comprising polymerizing the acrylic compound for a time and at least one temperature sufficient to react and form a polymer.

13. The method of claim 8 wherein the combining and the reacting steps are performed in the same reaction vessel.

14. The method of claim 8 wherein the combining step is conducted in the presence of a solvent.

15. The method of claim 8 wherein the reacting step is conducted in the presence of a base.

16. The method of claim 8 wherein the acylating agent is at least one selected from the group consisting of an anhydride, a chloride, a bromide, an ester, or an acid.

17. The method of claim 8 wherein a yield of the acrylic compound is at least about 80% of a theoretical yield.

18. The method of claim 17 wherein the yield of the acrylic compound is at least about 90% of the theoretical yield.

19. A polymer comprising polymerized units of the acrylic compound having the formula (I):

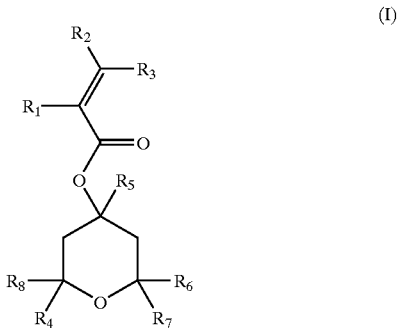

wherein R$_1$, R$_2$, and R$_3$ are each independently a hydrogen atom, a fluorine atom, an alkyl group, or a fluorinated alkyl group; R$_4$ is a hydroxyl group, an alkoxy group, a fluorinated alkoxy group, an acyloxy group, or a fluorine atom; R$_5$, R$_6$, R$_7$, and R$_8$ are each independently a fluorine atom, a fluorinated alkyl group having from 1 to 10 carbon atoms, an alkyl group, an alkenyl group, an alkynyl group, an aryl group, or an alkyl-substituted aryl group and at least one of R$_5$, R$_6$, R$_7$, and R$_8$ is a fluorinated alkyl group having from 1 to 10 carbon atoms; and wherein the alkyl group comprises from 1 to 20 carbons and the alkenyl and alkynyl groups comprise from 2 to 8 carbons.

20. The polymer of claim 19 further comprising polymerized units of at least one ethylenically unsaturated monomer.

21. A sub-200 nm photoresist composition comprising:

a polymer comprising one or more polymerized units of an acrylic compound of the formula (I):

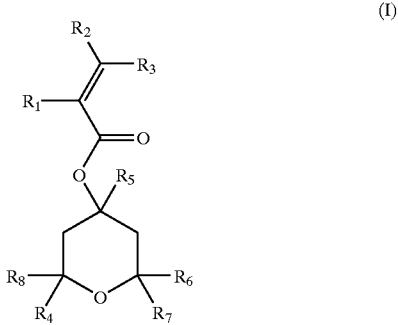

wherein $R_1$, $R_2$, and $R_3$ are each independently a hydrogen atom, a fluorine atom, an alkyl group, or a fluorinated alkyl group; $R_4$ is a hydroxyl group, an alkoxy group, a fluorinated alkoxy group, an acyloxy group, or a fluorine atom; $R_5$, $R_6$, $R_7$, and $R_8$ are each independently a fluorine atom, a fluorinated alkyl group having from 1 to 10 carbon atoms, an alkyl group, an alkenyl group, an alkynyl group, an aryl group, or an alkyl-substituted aryl group and at least one of $R_5$, $R_6$, $R_7$, and $R_8$ is a fluorinated alkyl group having from 1 to 10 carbon atoms; and wherein the alkyl group comprises from 1 to 20 carbons and the alkenyl and alkynyl groups comprise from 2 to 8 carbons; and a photoactive component.

22. The photoresist composition of claim 21 further comprising a solvent.

23. The photoresist composition of claim 21 wherein the photoactive component comprises a photoacid generator.

24. The photoresist composition of claim 23 wherein the photoacid generator is at least one selected from the group consisting of halogenated triazines, onium salts, sulfonated esters, halogenated sulfonyloxy dicarboximides, or mixtures thereof.

25. The photoresist composition of claim 21 wherein the polymer further comprises polymerized units of at least one ethylenically unsaturated monomer.

26. A polymer comprising repeating units of the following formula (II):

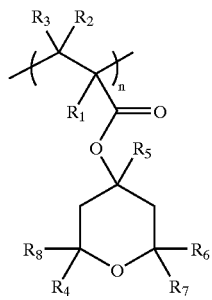

(II)

wherein $R_1$, $R_2$, and $R_3$ are each independently a hydrogen atom, a fluorine atom, an alkyl group, or a fluorinated alkyl group; $R_4$ is a hydroxyl group, an alkoxy group, a fluorinated alkoxy group, an acyloxy group, a fluorinated alkoxy group, an acyloxy group, or a fluorine atom; $R_5$, $R_6$, $R_7$, and $R_8$ are each independently a fluorine atom, a fluorinated alkyl group having from 1 to 10 carbon atoms, an alkyl group, an alkenyl group, an alkynyl group, an aryl group, or an alkyl-substituted aryl group and at least one of $R_5$, $R_6$, $R_7$, and $R_8$ is a fluorinated alkyl group having from 1 to 10 carbon atoms;

wherein the alkyl group comprises from 1 to 20 carbons and the alkenyl and alkynyl groups comprise from 2 to 8 carbons; and wherein n is a number ranging from 3 to 300.

* * * * *

UNITED STATES PATENT AND TRADEMARK OFFICE
CERTIFICATE OF CORRECTION

PATENT NO.     : 6,919,160 B2
DATED          : July 19, 2005
INVENTOR(S)    : Atteye Houssein Abdourazak and Thomas John Markley It is certified that error appears in the above-identified patent and that said Letters Patent is hereby corrected as shown below:

<u>Column 15,</u>
Line 3, delete the words "group comprises" and substitute therefore -- groups comprise --.

<u>Column 16,</u>
Line 44, delete the words "group comprises" and substitute therefore -- groups comprise --.

<u>Column 17,</u>
Line 11, delete the words "group comprises" and substitute therefore -- groups comprise --.

<u>Column 18,</u>
Line 26, delete the words "group comprises" and substitute therefore -- groups comprise --.

Signed and Sealed this

Sixth Day of September, 2005

JON W. DUDAS
*Director of the United States Patent and Trademark Office*